(12) United States Patent
Lee et al.

(10) Patent No.: US 10,889,673 B2
(45) Date of Patent: Jan. 12, 2021

(54) SUPER ABSORBENT POLYMER AND PREPARATION METHOD THEREOF

(71) Applicant: LG Chem, Ltd., Seoul (KR)

(72) Inventors: Sang Gi Lee, Daejeon (KR); Chul Hee Ryu, Daejeon (KR); Kyu Pal Kim, Daejeon (KR); Bhom Ri Kim, Daejeon (KR)

(73) Assignee: LG Chem, Ltd.

(*) Notice: Subject to any disclaimer, the term of this patent is extended or adjusted under 35 U.S.C. 154(b) by 327 days.

(21) Appl. No.: 16/158,582

(22) Filed: Oct. 12, 2018

(65) Prior Publication Data

US 2019/0040173 A1 Feb. 7, 2019

Related U.S. Application Data

(60) Division of application No. 14/932,570, filed on Nov. 4, 2015, now Pat. No. 10,150,829, which is a continuation-in-part of application No. PCT/KR2014/003821, filed on Apr. 30, 2014.

(30) Foreign Application Priority Data

May 13, 2013 (KR) .................. 10-2013-0053935
Apr. 29, 2014 (KR) .................. 10-2014-0051816

(51) Int. Cl.
| | |
|---|---|
| *C08F 220/06* | (2006.01) |
| *A61L 15/60* | (2006.01) |
| *B01J 20/26* | (2006.01) |
| *C08J 3/075* | (2006.01) |
| *C08L 101/14* | (2006.01) |
| *A61L 15/24* | (2006.01) |
| *C08J 3/24* | (2006.01) |
| *C08F 222/10* | (2006.01) |

(52) U.S. Cl.
CPC ............ *C08F 220/06* (2013.01); *A61L 15/24* (2013.01); *A61L 15/60* (2013.01); *B01J 20/267* (2013.01); *C08J 3/075* (2013.01); *C08J 3/245* (2013.01); *C08L 101/14* (2013.01); *B01J 2220/68* (2013.01); *C08F 222/1006* (2013.01); *C08J 2333/02* (2013.01)

(58) Field of Classification Search
CPC .... C08F 222/1006; C08F 220/06; C08J 3/245
See application file for complete search history.

(56) References Cited

U.S. PATENT DOCUMENTS

| | | | |
|---|---|---|---|
| 4,446,261 A | 5/1984 | Yamasaki et al. |
| 4,973,632 A | 11/1990 | Nagasuna et al. |
| 5,244,735 A | 9/1993 | Kimura et al. |
| 6,110,984 A | 8/2000 | Fujimaru et al. |
| 9,486,778 B2 | 11/2016 | Ryu et al. |
| 2003/0069359 A1 | 4/2003 | Torii et al. |
| 2009/0208748 A1 | 8/2009 | Torii et al. |
| 2010/0256308 A1 | 10/2010 | Takatori et al. |
| 2011/0301303 A1 | 12/2011 | Kim et al. |
| 2011/0313113 A1 | 12/2011 | Sakamoto et al. |
| 2013/0026412 A1 | 1/2013 | Machida et al. |
| 2014/0296465 A1 | 10/2014 | Sakamoto et al. |
| 2015/0087742 A1 | 3/2015 | Won et al. |

FOREIGN PATENT DOCUMENTS

| | | |
|---|---|---|
| CN | 1455802 A | 11/2003 |
| CN | 102317329 A | 1/2012 |
| EP | 2518092 A1 | 10/2012 |
| EP | 2557095 A1 | 2/2013 |
| EP | 2727953 A1 | 5/2014 |
| JP | S56161408 A | 12/1981 |
| JP | S57158209 A | 9/1982 |
| JP | S57198714 A | 12/1982 |
| JP | H05112654 A | 5/1993 |
| JP | H09-309916 A | 12/1997 |
| JP | 2877255 B2 | 3/1999 |
| JP | 2001220415 A | 8/2001 |
| JP | 2007-144423 A | 6/2007 |
| JP | 2009531467 A | 9/2009 |
| KR | 1998-032750 A | 7/1998 |
| KR | 20050038033 A | 4/2005 |
| KR | 20100087167 A | 8/2010 |
| KR | 20110134333 A | 12/2011 |
| KR | 20120132475 A | 12/2012 |

(Continued)

OTHER PUBLICATIONS

International Search Report from PCT/KR2014/003821, dated Aug. 27, 2014.
George G. Odian, "Principles of Polymerization." A Wiley-Interscience Publication, 1981, p. 203.
Reinhold Schwalm, "UV Coatings Basics, Recent Developments and New Applications." Elsevier Science, Dec. 21, 2006, p. 115.

(Continued)

*Primary Examiner* — Peter D. Mulcahy
(74) *Attorney, Agent, or Firm* — Lerner, David, Littenberg, Krumholz & Mentlik, LLP

(57) ABSTRACT

The present invention relates to a super absorbent polymer and a preparation method thereof, the super absorbent polymer including: surface cross-linked polymer particles prepared by surface cross-linking particles of a base resin, the base resin polymerized from a monomer composition including water-soluble ethylene-based unsaturated monomers having at least partially neutralized acidic groups; and a water-soluble component, wherein the water-soluble component has a weight average molecular weight of 150,000 to 300,000 g/mol. The super absorbent polymer may have high centrifuge retention capacity and excellent permeability at the same time, while having low content of the water-soluble component.

6 Claims, No Drawings

(56) References Cited

FOREIGN PATENT DOCUMENTS

| KR | 20130120400 A | 11/2013 |
|----|---------------|---------|
| WO | 2007047598 A1 | 4/2007  |
| WO | 2007099515 A2 | 9/2007  |
| WO | 2011126079 A1 | 10/2011 |

OTHER PUBLICATIONS

Extended Search Report from European Application No. 14797407.5, dated Oct. 28, 2016.
http://www.edana.org/docs/default-source/default-document-library/harmonized-test-methods---2012 edition—2.pdf; 2012.

SUPER ABSORBENT POLYMER AND PREPARATION METHOD THEREOF

CROSS-REFERENCE TO RELATED APPLICATIONS

The application is a divisional of U.S. application Ser. No. 14/932,570, filed on Nov. 4, 2015, which is a continuation-in-part of International Application No. PCT/KR2014/003821 filed on Apr. 30, 2014, which claims priority to Korean Patent Application No. 10-2013-0053935 filed on May 13, 2013 and Korean Patent Application No. 10-2014-0051816 filed on Apr. 29, 2014 the disclosures of which are incorporated herein by reference.

BACKGROUND OF THE INVENTION

(a) Field of the Invention

The present invention relates to a super absorbent polymer and a preparation method thereof.

(b) Description of the Related Art

A super absorbent polymer (SAP) is a synthetic polymeric material capable of absorbing water five hundred up to one thousand times the mass of its own. The SAP is called by different names according to the developers, for example, a super absorbency material (SAM), an absorbent gel material (AGM), and the like. Commercial productions of the SAP began for use in feminine hygiene napkins, nowadays, the use of SAP may be found in a very wide range of applications, including water combination soils for gardening, water-stop materials for engineering and construction, sheets for raising seeding, freshness-keeping agents in the food distribution field, and materials for sweating rooms, as well as personal hygiene products, such as disposable baby diapers.

Known preparation methods for SAP include an inverse suspension polymerization method or an aqueous solution polymerization method. The method using inverse suspension polymerization is disclosed in, for example, JP S-56-161408, JP S-57-158209 and JP S-57-198714. The method using aqueous solution polymerization includes several methods: a thermal polymerization method including polymerization of a hydrogel polymer by shearing and freezing in a kneading machine provided with several spindles, and a photopolymerization method using UV radiations on a high-concentration aqueous solution on a conveyer belt to perform both polymerization and drying at once.

Meanwhile, a water-soluble component, that is, a polymer which is not cross-linked in the preparation method of the super absorbent polymer, is produced. When the water-soluble component has a high content, a solution absorption capacity of the super absorbent polymer is improved; meanwhile, when the super absorbent polymer contacts a liquid, the super absorbent polymer is easily eluted to make a surface sticky or to have a negative effect on a skin to be contacted. In addition, when the water-soluble component has a high content, the eluted water-soluble component generally remains on the surface of the super absorbent polymer to make the super absorbent polymer sticky, such that permeability which is a capacity of rapidly delivering a solution to other super absorbent polymers is decreased.

Therefore, development of a super absorbent polymer having high absorbency and excellent permeability has been demanded.

SUMMARY OF THE INVENTION

The present invention has been made in an effort to provide a super absorbent polymer having high centrifuge retention capacity and excellent permeability at the same time.

An exemplary embodiment of the present invention provides a super absorbent polymer including: surface cross-linked polymer particles prepared by surface cross-linking particles of a base resin, the base resin polymerizing from a monomer composition including water-soluble ethylene-based unsaturated monomers having at least partially neutralized acidic groups; and a water-soluble component, wherein the water-soluble component has a weight average molecular weight of 150,000 to 300,000 g/mol.

In the super absorbent polymer, the water-soluble component measured by the EDANA WSP 270.2 method may have a content of 5 to 20 wt % based on the total weight of the super absorbent polymer.

In the super absorbent polymer, a centrifuge retention capacity measured by the EDANA WSP 241.2 method may be 20 to 35 g/g.

In the super absorbent polymer, an absorbency under load measured by the EDANA WSP 242.2 method may be 20 to 30 g/g.

In the super absorbent polymer, a permeability measured according to the following Equation 1 may be 10 to 150 seconds:

$$\text{Permeability (sec)} = T_1 - B \quad \text{[Equation 1]}$$

$T_1$ represents a time required for decreasing a liquid level height from 40 ml up to 20 ml under a load of 0.3 psi (106.26 g) in a chromatography tube in the presence of saline solution-absorbed super absorbent polymer, wherein the saline solution-absorbed super absorbed polymer is prepared by putting 0.2±0.0005 g of a classified sample (30 # to 50 #) (particles size ranging from 300 μm to 600 μm) of super absorbent polymer into the chromatography tube and adding saline solution so that the saline solution has a volume of 50 ml, and leaving the tube for 30 minutes prior to measuring $T_1$, and B represents a time required for decreasing a liquid level height from 40 ml up to 20 ml in a chromatography tube filled with saline solution under a load of 0.3 psi in the absence of the super absorbent polymer.

Another exemplary embodiment of the present invention provides a preparation method of a super absorbent polymer, including: preparing a monomer composition including a water-soluble ethylene-based unsaturated monomers have un-neutralized acidic groups, and a polymerization initiator, wherein the polymerization initiator has a content of 40 to 300 ppm based on the amount of water-soluble ethylene-based unsaturated monomers; adding a neutralizing agent to the monomer composition to neutralize at least some of the un-neutralized acidic groups of the water-soluble ethylene-based unsaturated monomers; preparing a hydrogel polymer by polymerizing the monomer composition, wherein a polymerization temperature ranges from 20 to 45° C.; drying the hydrogel polymer; pulverizing the dried polymer to form particles; and surface cross-linking the particles in the presence of a surface cross-linking agent to form surface cross-linked polymer particles of the super absorbent polymer, wherein the surface cross-linking agent is present in an amount ranging from 0.15 to 0.7 wt % based on an amount of the particles.

A water-soluble component included in the super absorbent polymer may have a weight average molecular weight of 150,000 to 300,000 g/mol.

The super absorbent polymer according to the present invention may have high centrifuge retention capacity and excellent permeability at the same time, while having low content of the water-soluble component.

DETAILED DESCRIPTION OF THE EMBODIMENTS

Although the present invention can be modified variously and have several embodiments, the exemplary embodiments are illustrated in the accompanying drawings and will be described in detail in the detailed description. However, the present invention is not limited to the specific embodiments and should be construed as including all the changes, equivalents, and substitutions included in the spirit and scope of the present invention. Further, when it is determined that the detailed description of the known art related to the present invention may obscure the gist of the present invention, the detailed description thereof will be omitted.

The present invention provides a super absorbent polymer including: surface cross-linked polymer particles prepared by surface cross-linking particles of a base resin, the base resin polymerizing from a monomer composition including water-soluble ethylene-based unsaturated monomers having at least partially neutralized acidic groups; and a water-soluble component, wherein the water-soluble component has a weight average molecular weight of 150,000 to 300,000 g/mol.

In addition, the present invention provides a preparation method of a super absorbent polymer, including: preparing a monomer composition including a water-soluble ethylene-based unsaturated monomers have un-neutralized acidic groups, and a polymerization initiator, wherein the polymerization initiator has a content of 40 to 300 ppm based on the amount of water-soluble ethylene-based unsaturated monomers; adding a neutralizing agent to the monomer composition to neutralize at least some of the un-neutralized acidic groups of the water-soluble ethylene-based unsaturated monomers; preparing a hydrogel polymer by polymerizing the monomer composition, wherein a polymerization temperature ranges from 20 to 45° C.; drying the hydrogel polymer; pulverizing the dried polymer to form particles; and surface cross-linking the particles in the presence of a surface cross-linking agent to form surface cross-linked polymer particles of the super absorbent polymer, wherein the surface cross-linking agent is present in an amount ranging from 0.15 to 0.7 wt % based on an amount of the particles.

Hereinafter, a super absorbent polymer according to an exemplary embodiment of the present invention and a preparation method of the super absorbent polymer are described in more detail.

According to an exemplary embodiment of the present invention, there is provided a super absorbent polymer including: surface cross-linked polymer particles prepared by surface cross-linking particles of a base resin, the base resin polymerizing from a monomer composition including water-soluble ethylene-based unsaturated monomers having at least partially neutralized acidic groups; and a water-soluble component, wherein the water-soluble component has a weight average molecular weight of 150,000 to 300,000 g/mol.

The water-soluble component generally has various molecular weight distributions, and in the present invention, a molecular weight of the water-soluble component indicates a weight average molecular weight thereof.

The water-soluble component, that is, a polymer which is not cross-linked in the preparation method of the super absorbent polymer, is produced. When the water-soluble component has a high content, an absorption capacity of the super absorbent polymer is improved; meanwhile, when contacting a liquid, the super absorbent polymer is easily eluted to make a surface of a diaper, and the like, sticky or to damage a skin, and the like. Meanwhile, when the water-soluble component has a high content, the eluted water-soluble component generally remains on the surface of the super absorbent polymer to make the super absorbent polymer sticky, such that permeability is decreased. The absorbency and permeability are opposite properties, and the super absorbent polymer having both of improved absorbency and permeability may exhibit significantly excellent physical properties. In particular, for example, when considering recent trend that the diaper has a slim thickness, these properties become significantly important.

Meanwhile, during the polymerization, cross-linkage of the water-soluble component of the super absorbent polymer is not complete, such that the water-soluble component may be present in a state that the water-soluble component is not cross-linked. However, the water-soluble component may be generally generated by decomposition of a cross-linking agent or break of a main polymer chain in a drying process. In this case, a dangling chain of which one side is cross-linked but the other side is not cross-linked to have a free polymer chain form, rather than the cross-linked chain, is eluted as the water-soluble component, when the polymer chain is decomposed by heat.

The present invention provides the super absorbent polymer in which the water-soluble component has a weight average molecular weight of 150,000 to 300,000 g/mol, or 150,000 to 250,000 g/mol, or 180,000 to 250,000 g/mol, or 200,000 to 250,000 g/mol, in order to provide the super absorbent polymer having high centrifuge retention capacity and excellent permeability while including a low content of the water-soluble component, considering that a molecular weight distribution of the eluted water-soluble component as well as the content of the water-soluble component have an effect on absorbency and permeability.

In the super absorbent polymer, the water-soluble component measured by the EDANA WSP 270.2 method may have a content of 5 to 20 wt %, or 5 to 15 wt %, or 5 to 12 wt %, or 9 to 12 wt % based on the total weight of the super absorbent polymer.

In addition, in the super absorbent polymer, the centrifuge retention capacity measured by the EDANA WSP 241.2 method may be 20 to 35 g/g, or 25 to 35 g/g, or 30 to 35 g/g.

Further, in the super absorbent polymer, the absorbency under load measured by the EDANA WSP 242.2 method may be 20 to 30 g/g, or 20 to 28 g/g, or 22 to 26 g/g.

In addition, in the super absorbent polymer, the permeability (sec) measured according to the following Equation 1 may be 10 to 150 seconds, or 20 to 120 seconds, or 50 to 120 seconds, or 80 to 120 seconds.

$$\text{Permeability (sec)} = T1 - B \quad \text{[Equation 1]}$$

T1 represents a time required for decreasing a liquid level height from 40 ml up to 20 ml under a load of 0.3 psi (106.26 g) in a chromatography tube in the presence of saline solution-absorbed super absorbent polymer, wherein the saline solution-absorbed super absorbed polymer is prepared by putting 0.2±0.0005 g of a classified sample (30 # to 50 #) (particles size ranging from 300 μm to 600 μm) of super absorbent polymer into the chromatography tube and adding saline solution so that the saline solution has a volume of 50 ml, and leaving the tube for 30 minutes prior to measuring T1, and B represents a time required for decreasing a liquid level height from 40 ml up to 20 ml in a chromatography tube filled with saline solution under a load of 0.3 psi in the absence of the super absorbent polymer.

According to an exemplary embodiment of the present invention, the present invention provides a preparation method of a super absorbent polymer, including: preparing a monomer composition including a water-soluble ethylene-based unsaturated monomers have un-neutralized acidic groups, and a polymerization initiator, wherein the polymerization initiator has a content of 40 to 300 ppm based on the amount of water-soluble ethylene-based unsaturated monomers; adding a neutralizing agent to the monomer composition to neutralize at least some of the un-neutralized acidic groups of the water-soluble ethylene-based unsaturated monomers; preparing a hydrogel polymer by polymerizing the monomer composition, wherein a polymerization temperature ranges from 20 to 45° C.; drying the hydrogel polymer; pulverizing the dried polymer to form particles; and surface cross-linking the particles in the presence of a surface cross-linking agent to form surface cross-linked polymer particles of the super absorbent polymer, wherein the surface cross-linking agent is present in an amount ranging from 0.15 to 0.7 wt % based on an amount of the particles.

The water-soluble component included in the super absorbent polymer prepared according to the preparation method as described above may have a weight average molecular weight of 150,000 to 300,000 g/mol, or 150,000 to 250,000 g/mol, or 180,000 to 250,000 g/mol or 200,000 to 250,000 g/mol.

In addition, in the super absorbent polymer prepared according to the preparation method as described above, the water-soluble component measured by the EDANA WSP 270.2 method may have a content of 5 to 20 wt %, or 5 to 15 wt %, or 5 to 12 wt %, or 9 to 12 wt % based on the total weight of the super absorbent polymer.

The water-soluble component has a large difference in an overall content of the water-soluble component and a molecular weight of the water-soluble component depending on a content of an initiator to be used at the time of polymerization, a polymerization temperature, and a content of a cross-linking agent, and as the content of the initiator becomes decreased, and the polymerization temperature becomes decreased, and the content of the cross-linking agent becomes increased, it is general to decrease the molecular weight of the water-soluble component.

Meanwhile, since the molecular weight and the content of the water-soluble component are related with various process conditions as described above, it is not easy to obtain optimized molecular weight and content of the water-soluble component by controlling various variables. However, according to the preparation method of the present invention, the present inventors found the weight average molecular weight and content ranges of the water-soluble component balancing the centrifuge retention capacity and the permeability by controlling the content of the polymerization initiator, and the polymerization temperature at the time of preparing the hydrogel polymer, and the content of the surface cross-linking agent at the time of performing surface cross-linking on the polymer within optimized ranges, respectively, and therefore, the super absorbent polymer having high centrifuge retention capacity and excellent permeability at the same time could be obtained, then completed the present invention.

According to an exemplary embodiment of the present invention, a monomer composition including a water-soluble ethylene-based unsaturated monomers and a polymerization initiator is prepared, and a hydrogel polymer is prepared by polymerizing the monomer composition.

In the above-description, in the polymerizing of the monomer composition, the polymerization initiator may have a content of 40 to 300 ppm or 50 to 200 ppm on the basis of the water-soluble ethylene-based unsaturated monomers, the polymerization temperature (temperature of the monomer during the polymerization) may be 20 to 45° C., or 25 to 40° C., and the surface cross-linking agent may have a content of 0.15 to 0.7 wt %, or 0.2 to 0.5 wt % based on the amount of the particles.

As described above, when all of the content of the polymerization initiator, the polymerization temperature, and the content of the surface cross-linking agent in the preparation method of the super absorbent polymer satisfy the above-described ranges, respectively, the weight average molecular weight and the content of the water-soluble component included in the super absorbent polymer to be obtained may satisfy the above-described ranges.

In addition, the polymerization initiator may be at least one selected from the group consisting of a thermal polymerization initiator, a redox initiator, and a photopolymerization initiator.

In the preparation method according to the exemplary embodiment of the present invention, the polymerization initiator is used. According to the polymerization method, the photopolymerization initiator may be used in the photopolymerization method, and the thermal polymerization initiator may be used in the thermal polymerization method. Meanwhile, in the photopolymerization method, the thermal polymerization initiator may be additionally included since a predetermined amount of heat occurs by ultraviolet irradiation, and the like, and in addition, as the polymerization reaction which is an exothermic reaction is performed, some degree of heat occurs.

Specific examples of the thermal polymerization initiator may include at least one selected from the group consisting of a persulfate-based initiator, an azo-based initiator, hydrogen peroxide, and an ascorbic acid. Specifically, examples of the persulfate-based initiator may include sodium persulfate ($Na_2S_2O_8$), potassium persulfate ($K_2S_2O_8$), ammonium persulfate (($NH_4)_2S_2O_8$), and the like, and examples of the azo-based initiator may include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid), and the like. More various thermal initiators are specified in "Principle of Polymerization (Wiley, 1981)", page 203, written by Odian. However, the present invention is not limited to the above-described examples.

Meanwhile, examples of the photopolymerization initiator may include at least one selected from the group consisting of benzoin ether, dialkyl acetophenone, hydroxyl alkylketone, phenyl glyoxylate, benzyl dimethyl ketal, acyl phosphine, and α-aminoketone. Meanwhile, specific examples of acyl phosphine may include commercially available lucirin TPO, that is, 2,4,6-trimethyl-benzoyl-trimethyl phosphine oxide. More various photopolymerization initiators are specified in "UV Coatings: Basics, Recent Developments and New Application (Elsevier, 2007)", page 115, written by Reinhold Schwalm. However, the present invention is not limited to the above-described examples.

In addition, the water-soluble ethylene-based unsaturated monomers may be at least one selected from the group consisting of acrylic acid (also salts thereof), acrylate, and methacrylic acid (also salts thereof) including unsaturated hydrocarbons. The water-soluble ethylene-based unsaturated monomers may have un-neutralized acidic groups.

Further, the water-soluble ethylene-based unsaturated monomers may be used without a limitation in view of a configuration as long as it is a monomer generally used in preparation of the super absorbent polymer. The water-soluble ethylene-based unsaturated monomers may largely include at least any one selected from the group consisting of anionic monomers and their salts, nonionic hydrophilic-containing monomers, or unsaturated monomers containing amino groups and their quarternary compounds.

More specifically, the water-soluble ethylene-based unsaturated monomers preferably include at least any one selected from the group consisting of anionic monomers (e.g., acrylic acid, methacrylic acid, anhydrous maleic acid, fumaric acid, crotonic acid, itacronic acid, 2-acryloyl ethane sulfonic acid, 2-methacryloyl ethane sulfonic acid, 2-(meta)acryloyl propane sulfonic acid, or 2-(meta)acrylamide-2-methyl propane sulfonic acid) and their salts; nonionic hydrophilic-containing monomers (e.g., (meta)acrylamide, N-substituted(meta)acrylate, 2-hydroxyethyl(meta)acrylate, 2-hydroxypropyl(meta)acrylate, methoxypolyethylene glycol(meta)acrylate, or polyethylene glycol(meta)acrylate); and unsaturated monomers containing amino groups (e.g., (N,N)-dimethylaminoethyl(meta)acrylate, or (N,N)-dimethylaminopropyl(meta)acrylamide) and their quarternary compounds.

More preferably, the acrylic acid or salts thereof may be used as the monomer. When the acrylic acid or salts thereof are used as the monomer, the super absorbent polymer, particularly, having improved absorptiveness may be obtained.

Meanwhile, a concentration of the water-soluble ethylene-based unsaturated monomers in the monomer composition may be appropriately selected in consideration of a polymerization time, a reaction condition, and the like. Preferably, the concentration of the water-soluble ethylene-based unsaturated monomers may be 40 to 55 wt %. When the concentration of the water-soluble ethylene-based unsaturated monomers is less than 40 wt %, it is not effective in view of economic feasibility, and when the concentration of the water-soluble ethylene-based unsaturated monomers is more than 55 wt %, at the time of pulverizing the polymerized hydrogel polymer, a pulverization efficiency may be decreased.

Before polymerizing the monomer composition, a neutralizing agent may be added to the monomer composition to neutralize at least some of the un-neutralized acidic groups of the water-soluble ethylene-based unsaturated monomers.

In addition, the monomer composition may be polymerized by solution polymerization.

The polymerization method in the preparing of the hydrogel polymer by thermal polymerizing or photopolymerizing the monomer composition is not limited in view of a configuration as long as it is a generally used polymerization method. Specifically, the polymerization method is largely classified into a thermal polymerization and a photopolymerization according to a polymerization energy source. The thermal polymerization may be generally performed in a reactor such as a kneader having stirring spindles, and the photopolymerization may be performed in the reactor provided with a movable conveyer belt. However, these polymerization methods are provided as an example, and the present invention is not limited to the above-described polymerization methods.

As an example, the hydrogel polymer obtained by thermal polymerization by supplying hot air in the reactor such as the kneader having stirring spindles as described above or by heating the reactor, or discharged from an outlet of the reactor may have a few centimeters to a few millimeters according to the shape of the stirring spindles provided in the reactor. Specifically, a size of the obtained hydrogel polymer may vary according to a concentration and an injection rate of the monomer composition to be injected, and in general, the hydrogel polymer may have a weight average particle diameter of 2 to 50 mm.

In addition, when the photopolymerization is performed in the reactor provided with the movable conveyer belt as described above, the generally obtained hydrogel polymer may be a sheet-shaped hydrogel polymer having a width of the belt. Here, the thickness of the polymer sheet may vary according to the concentration and the injection rate of the monomer composition to be injected; however, it is preferred to supply the monomer composition so as to obtain the sheet-shaped polymer having a thickness of 0.5 to 5 cm. When supplying the monomer composition so that the sheet-shaped polymer has an extremely thin thickness, a production efficiency may be low, which is not preferred, and when a thickness of the sheet-shaped polymer is more than 5 cm, the polymerization reaction may not be uniformly performed throughout an overall thickness due to the extremely thick thickness.

Meanwhile, the hydrogel polymer right after the polymerization is subjected to a drying process. It is preferred that a drying temperature of the drying process is 150° C. to 250° C. Meanwhile, "the drying temperature" throughout the specification may be defined as a temperature of a thermal media supplied for drying or a temperature of a drying reactor including the thermal media and the polymer in the drying process.

When the drying temperature is less than 150° C., a drying time may be extremely increased, and thus physical properties of the finally formed super absorbent polymer may be deteriorated, and when the drying temperature is more than 250° C., only a surface of the polymer may be extremely dried, such that fine powder may occur in a pulverization process to be performed later and physical properties of the finally formed super absorbent polymer may be deteriorated. Preferably, the drying process may be performed at a temperature of 150° C. to 200° C., and more preferably, at a temperature of 160° C. to 180° C.

Meanwhile, the drying time is not limited in view of a configuration, for example, may be 20 minutes to 90 minutes in consideration of a process efficiency, and the like.

In addition, the drying method of the drying process may also be selected without limitation in view of a configuration as long as it is generally used as a drying process of the hydrogel polymer. Specifically, the drying process may be performed by hot air supply, infrared irradiation, microwave irradiation, ultraviolet irradiation, or the like. The polymer after performing the drying process may have a percentage of water content of 0.1 to 10 wt %.

Then, the dried polymer is pulverized to form particles of the super absorbent polymer. The super absorbent polymer or particles of the super absorbent polymer before performing surface cross-linking may be referred to as a base resin.

Meanwhile, in order to perform surface cross-linking on the particles, the surface cross-linking agent may be added. Here, the surface cross-linking agent which is usable is not limited in view of a configuration as long as it is a compound which is capable of reacting with functional groups of the particles.

Preferably, in order to improve properties of the super absorbent polymer to be produced, examples of the surface cross-linking agent may include at least one selected from group consisting of polyvalent alcohol compounds; epoxy compounds; polyamine compounds; halo epoxy compounds; condensation products of halo epoxy compounds; oxazoline compounds; mono-, di- or poly-oxazolidinone compounds; annular urea compounds; polyvalent metal salts; and alkylene carbonate compounds.

Specifically, examples of the polyvalent alcohol compound may include at least one selected from the group consisting of mono-, di-, tri-, tetra- or polyethylene glycol, mono propylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

In addition, examples of the epoxy compound may include ethylene glycol diglycidyl ether and glycidol, and examples of the polyamine compound may include at least one selected from the group consisting of ethylenediamine, diethylenetriamine, triethylenetetramine, tetraethylenepentamine, pentaethylenehexamine, polyethyleneimine, and polyamidepolyamine.

Further, examples of haloepoxy compound may include epichlorohydrin, epibromohydrin and α-methyl epichlorohydrin. Meanwhile, examples of the mono-, di- or poly-oxazolidinone compound may include 2-oxazolidinone, and the like.

In addition, examples of the alkylene carbonate compound may include ethylene carbonate, and the like. The above-described compounds may be used alone, respectively, or may be combined with each other. Meanwhile, in order to increase an efficiency of the surface cross-linking process, it is preferred to include at least one polyvalent alcohol compounds in the surface cross-linking agent, and more preferably, C2 to C10 polyvalent alcohol compounds may be used.

According to the preparation method of the present invention, the surface cross-linking agent which is added to the particles as described above may have a content of 0.15 to 0.7 wt %, preferably, 0.2 to 0.5 wt % on an amount of the pulverized particles. When the surface cross-linking agent has the above-described ranged content, the weight average molecular weight and the content of the water-soluble component according to the present invention may be obtained.

Here, the method of adding the surface cross-linking agent to the particles is not limited in view of a configuration. There are a method of putting the surface cross-linking agent and the particles into a reaction bath and mixing the agent with the particles, a method of spraying the surface cross-linking agent onto the particles, and a method of continuously supplying the polymer and the cross-linking agent into a continuously operated mixer and mixing the agent with the particles.

In addition, when adding the surface cross-linking agent, water may be additionally added. When adding water, the surface cross-linking agent may be uniformly dispersed in the polymer. Here, the content of water to be added is preferably 0.5 to 10 parts by weight on the basis of 100 parts by weight of the polymer in order to induce uniform dispersion of the surface cross-linking agent, to prevent agglomeration phenomenon of the particles, and to optimize a depth at which the cross-linking agent is permeated onto a surface.

Meanwhile, according to another exemplary embodiment of the present invention, in order to raise a temperature to the reaction temperature for the surface cross-liking at a rate of 3° C./min to 15° C./min after adding the surface cross-linking agent, the temperature of particles itself is preferably 20° C. to 90° C. at the time of adding the surface cross-linking agent. In order to have the temperature of the particles itself as described above, processes to be performed after the drying process to be performed at a relatively high temperature may be continuously performed, or processing time may be reduced, or when it is difficult to reduce the processing time, the particles may be separately heated.

In addition, according to another exemplary embodiment of the present invention, in order to raise a temperature to the reaction temperature for the surface cross-liking at a rate of 3° C./min to 15° C./min after adding the surface cross-linking agent, the surface cross-linking agent itself to be added to the particles may be heated.

Preferably, the temperature of the surface cross-linking agent to be added is 10° C. to 90° C., and more preferably, 20° C. to 60° C. When the temperature of the surface cross-linking agent is less than 10° C., an effect of reducing the raising rate of the temperature to the reaction temperature for the surface cross-linking according to the raise in temperature of the surface cross-linking agent may not be sufficient, and when the temperature of the surface cross-linking agent is more than 90° C., the surface treatment agent may not be uniformly mixed.

In addition, the means of raising the temperature for the surface cross-linking reaction are not limited in view of a configuration. The temperature may be raised by supplying the thermal media or directly supplying heat source. Here, examples of the usable thermal media may include temperature-raising fluids such as steam, hot air and hot oil. However, the present invention is not limited to the above-described examples. In addition, a temperature of the supplied thermal media may be appropriately selected in consideration of the means of thermal media, the raising rate of the temperature, and target temperature in raising temperature. Meanwhile, examples of heat source to be directly supplied may include electricity and gas. However, the present invention is not limited to the above-described examples.

It is preferred to use the thermal media over 100° C. by considering that the temperature of the surface cross-linking is 100 to 250° C., and the thermal media having an appropriate temperature over 100° C. may be selected in consideration of the raising rate of the temperature, volume of the reactor, and the kinds of the thermal media.

Meanwhile, after the raising of the temperature for the cross-linking is performed, the cross-linking reaction may be performed for 1 min to 120 mins, preferably, 1 min to 60 mins, and most preferably, 10 mins to 50 mins.

When the time for the cross-linking reaction is excessively decreased to be less than 1 min, sufficient cross-linking reaction may not be performed, and when the time for the cross-linking reaction is more than 120 mins, due to excessive surface cross-linking reaction, physical properties may be deteriorated by damage of the polymer particles.

Hereinafter, exemplary embodiments of the present invention will be described in detail. However, these examples are only to illustrate the present invention and the scope of the present invention is not construed to be limited to these examples.

Example 1

A solution (A solution) obtained by mixing 500 g of acrylic acid with 11 g of 1% IRGACURE 819 initiator diluted in acrylic acid and mixing the reaction mixture with 38 g of diluted 5% polyethylene glycol diacrylate (PEGDA, molecular weight 400) was injected into a 2 L glass reactor enclosed with a jacket in which thermal media pre-cooled at 25° C. was circulated, and 800 g of 24% sodium hydroxide solution (B solution) was slowly added dropwise, then mixed with together.

After confirming that a temperature of the mixed solution was raised to be over 80° C. by heat of neutralization at the time of mixing two solutions and waiting that the reaction temperature was cooled to 40° C., when the reaction temperature arrived at 40° C., 54 g of 2% sodium persulfate solution diluted with water was injected thereinto.

The solution was poured into a tray (length: 15 cm×width: 15 cm) in a Vat shape installed in a square polymerization reactor having a photo irradiation device mounted thereon and an inner part preheated to 80° C. to perform photo irradiation, such that photo initiation was conducted. It was confirmed that after about 25 seconds from the photo irradiation, gel was generated from a surface, and after about 50 seconds, the polymerization reaction was generated while simultaneously generating foams. Then, after additional reaction was performed for 3 minutes, the polymerized sheet was cut into a size of 3×3 cm and chopped by a meat chopper to prepare crumbs of hydrogel polymers.

The crumbs were dried in an oven in which air flow transition is vertically possible. The crumbs were uniformly dried by allowing hot air at 180° C. flow from bottom to top for 15 minutes and from top to bottom for 15 minutes so that the dried polymers had a content of 2% or less after the drying process.

After drying, the polymers were pulverized by a pulverizer, and were subjected to classification and screening to a size of 150 to 850 μm to prepare a base resin. The prepared base resin had a centrifuge retention capacity of 38.5 g/g, and a content of the water-soluble component of 13.2 wt %.

Next, surface cross-linking was performed on the base resin using 3% ethylene glycol diglycidyl ether solution to react at 120° C. for 1 hour. Then, after pulverization, the surface treated super absorbent polymer having a particle size of 150 to 850 μm was obtained using sieve.

Example 2

A super absorbent polymer of Example 2 was obtained by performing the same process as Example 1 except for mixing with 55 g of diluted 5% polyethylene glycol diacrylate (PEGDA, molecular weight 400). Here, the prepared base resin had a centrifuge retention capacity of 36.2 g/g, and a content of the water-soluble component of 11.3 wt %.

Example 3

A super absorbent polymer was obtained by performing surface cross-linking on the base resin obtained by Example 1. The surface cross-linking was performed by uniformly distributing 6.3 g of a cross-linking agent on the base resin, the cross-linking agent containing 3.3% of 1,3-propanediol in a mixed solution containing water and methanol (a ratio between water and methanol is a weight ratio of 1:1) on the basis of 100 g of the base resin, and stirring for 1 minute by a high speed mixer to mix together, then, putting the mixture into a stirring bath having a heat jacket to react each other at a temperature of 185° C. for 50 mins After the reaction, the super absorbent polymer was pulverized to obtain the surface treated super absorbent polymer having a particle size of 150 to 850 μm using sieve.

Example 4

A super absorbent polymer was obtained by performing the same process as Example 3 except for adding 0.3 wt % of aluminum sulfate to the surface cross-linking agent in the surface cross-linking.

Comparative Example 1

A solution (A solution) obtained by mixing 450 g of acrylic acid with 9 g of 10% tetraethylene glycol diacrylate (TEGDA) diluted in acrylic acid was injected into a 2 L glass reactor enclosed with a jacket in which thermal media pre-cooled at 60° C. was circulated, and 750 g of 25% sodium hydroxide solution (B solution) was slowly added dropwise, then mixed with together.

After confirming that a temperature of the mixed solution was raised to be over 80° C. by heat of neutralization at the time of mixing two solutions and waiting that the reaction temperature was cooled to 80° C., when the reaction temperature arrived at 80° C., 22.5 g of 10% sodium persulfate solution diluted with water was injected thereinto.

It was confirmed that after the sodium persulfate was injected and stirred for several seconds, the polymerization began immediately. It was confirmed that at an initial stage, the mixture was clear, but became gradually opaque, and when the gel was formed in the reactor, the stirring was stopped and the polymer polymerization including foam generation was actively conducted. It was confirmed that a volume expansion rate at the foam generation was increased 30 times or more than the volume of the initially injected monomer solution.

After 3 minutes, the foam was slowly decreased and the hydrogel polymer could be obtained. The polymer was cut into a size of 3×3 cm and chopped by a meat chopper to prepare crumbs of hydrogel polymer.

The crumbs were dried in an oven in which air flow transition is vertically possible. The crumbs were uniformly dried by allowing hot air at 180° C. flow from bottom to top for 15 minutes and from top to bottom for 15 minutes so that the dried polymers had a content of 2% or less after the drying process.

After drying, the polymers were pulverized by a pulverizer, and were subjected to classification and screening to a size of 150 to 850 μm to prepare a base resin. Here, the prepared base resin had a centrifuge retention capacity of 40.3 g/g, and a content of the water-soluble component of 14.5 wt %.

Next, surface cross-linking was performed on the base resin using 3% ethylene glycol diglycidyl ether solution and reacted at 120° C. for 1 hour. Then, after pulverization, the surface treated super absorbent polymer having a particle size of 150 to 850 μm was obtained using sieve.

Comparative Example 2

A super absorbent polymer was obtained by performing surface cross-linking on the base resin obtained by Comparative Example 1. The surface cross-linking was performed by uniformly distributing 5 g of a cross-linking agent on the base resin, the cross-linking agent containing 4.2% of 1,3-propanediol in a mixed solution containing water and methanol (a ratio between water and methanol is a weight ratio of 1:1.1) on the basis of 100 g of the base resin, and stirring for 1 minute by a high speed mixer to mix together, then, putting the mixture into a stirring bath having a heat jacket to react each other at a temperature of 185° C. for 50 mins. After the reaction, the super absorbent polymer was pulverized to obtain the surface treated super absorbent polymer having a particle size of 150 to 850 μm using sieve.

Comparative Example 3

A super absorbent polymer was obtained by performing the same process as Comparative Example 2 except for adding 0.3 wt % of aluminum sulfate to the surface cross-linking agent in the surface cross-linking.

Physical properties of the super absorbent polymers prepared according to Examples and Comparative Examples were measured as follows and the results thereof were shown in Table 1.

Test Example 1: Measurement of Centrifuge Retention Capacity

A centrifuge retention capacity of the super absorbent polymer particles prepared according to Examples and Comparative Examples was measured by the EDANA WSP 241.2 method.

The centrifuge retention capacity was measured by putting 0.2 g of the sample classified to 30 to 50 mesh into tea bags, keeping the sample soaked in 0.9% saline solution for 30 minutes, removing water in a centrifuge set to 250 G for 3 minutes, and measuring weight so as to measure an amount of water retained in the super absorbent polymer.

Test Example 2: Measurement of Water-Soluble Component

Water-soluble component of super absorbent polymer particles prepared according to Examples and Comparative Examples was measured by the EDANA WSP 270.2 method. 1.0 g of the sample classified to 30 to 50 mesh were put into 200 g of 0.9% saline solution, and kept to be soaked for 16 hours while stirring at 500 rpm, and each aqueous solution was filtrated by a filter paper. Each filtrated solution was primarily titrated with sodium hydroxide solution (pH 10.0), reverse-titrated with a hydrogen chloride solution (pH 2.7), and as the water-soluble component, the polymer material which was not cross-linked was calculated from the amount required for the neutralization.

Test Example 3: Measurement of Average Molecular Weight of Water-Soluble Component Weight average molecular weight of the water-soluble components of the super absorbent polymers prepared according to Examples and Comparative Examples was measured. 1.0 g of the sample classified to 30 to 50 mesh were put into 200 g of 0.9% saline solution, and kept to be soaked for 16 hours while stirring at 500 rpm, and the aqueous solution was filtrated by a filter paper. Each filtrated solution was separated by gel permeation chromatograph (GPC) column for measurement.

GPC was performed on an instrument manufactured by Wyatt DAWN EOS, Wyatt Optilab DSP, Waters, or Wyatt using Ultrahydrogel Linear X2 as a column, 0.1 M $NaNO_3$/ 0.02 M phosphate buffer as a solvent under the conditions of a flow rate of 0.8 mL/min and a temperature of 60° C., and polyacrylic acid was used as a standard.

Test Example 4: Measurement of Permeability

Lines were marked on liquid level height of 20 ml and 40 ml in a state in which piston was put into a chromatography tube (F20 mm). Then, water was injected reversely up to about 10 ml so that foams between a glass filter and a cock at a low part of the chromatography tube were not generated, then the chromatography tube was washed with saline solution two or three times, and filled with 0.9% saline solution up to 40 ml or more. The piston was put into the chromatography tube and a lower valve was opened, then, a time (B) required for decreasing the liquid level height from 40 ml up to 20 ml was recorded.

The classified sample (30 # to 50 #) having 0.2±0.0005 g was put into the chromatography tube filled with 10 ml of saline solution, then, saline solution was added to have a volume of 50 ml, and then left for 30 minutes. Then, after a piston (0.3 psi=106.26 g) with a weight was put into the chromatography tube, the tube was left for 1 minute, then, a lower valve of the chromatography tube was opened, and a time (T1) required for decreasing a liquid level height from 40 ml up to 20 ml was recorded to calculate a time of T1-B.

TABLE 1

| | Super Absorbent Polymer | | | | |
|---|---|---|---|---|---|
| | Centrifuge retention capacity (g/g) | Absorbency under load (g/g) | Permeability (sec) | Water-Soluble Component (%) | Weight Average Molecular Weight of Water-Soluble Component |
| Example 1 | 34.5 | 24.5 | 85 | 13.2 | 250,000 |
| Example 2 | 33.5 | 25.1 | 97 | 11.3 | 220,000 |
| Example 3 | 34.2 | 23.8 | 115 | 9.7 | 236,000 |
| Example 4 | 32.7 | 25.5 | 52 | 10.2 | 187,000 |
| Comparative Example 1 | 33.7 | 24.4 | 165 | 14.5 | 140,000 |
| Comparative Example 2 | 32.1 | 23.6 | 183 | 12.4 | 125,000 |
| Comparative Example 3 | 31.8 | 22.7 | 78 | 13.6 | 132,000 |

The present invention has been described in detail based on particular features thereof, and it is obvious to those skilled in the art that these specific technologies are merely preferable embodiments and thus the scope of the present invention is not limited to the embodiments. Therefore, the substantial scope of the present invention will be defined by the accompanying claims and their equivalents.

What is claimed is:

1. A preparation method of a super absorbent polymer, comprising:
    preparing a monomer composition including a water-soluble ethylene-based unsaturated monomers have unneutralized acidic groups, and a polymerization initiator, wherein the polymerization initiator has a content of 40 to 300 ppm based on the amount of water-soluble ethylene-based unsaturated monomers;

adding a neutralizing agent to the monomer composition to neutralize at least some of the un-neutralized acidic groups of the water-soluble ethylene-based unsaturated monomers;
preparing a hydrogel polymer by polymerizing the monomer composition, wherein a polymerization temperature ranges from 20 to 45° C.;
drying the hydrogel polymer;
pulverizing the dried polymer to form particles; and
surface cross-linking the particles in the presence of a surface cross-linking agent to form surface cross-linked polymer particles of the super absorbent polymer, wherein the surface cross-linking agent is present in an amount ranging from 0.15 to 0.7 wt % based on an amount of the particles.

2. The preparation method of claim 1, wherein the super absorbent polymer includes a water-soluble component included in the super absorbent polymer has a weight average molecular weight of 150,000 to 300,000.

3. The preparation method of claim 1, wherein the surface crosslinking is performed at temperatures ranging from about 120 to about 185 degrees Celsius.

4. The preparation method of claim 1, wherein preparing the monomer composition further comprises:
adding an internal cross linking agent.

5. The preparation method of claim 1, wherein the surface cross-linking agent includes aluminum sulfate.

6. The preparation method of claim 1, wherein the super absorbent polymer comprising:
surface cross-linked polymer particles prepared by surface cross-linking particles of a base resin, the base resin polymerized from a monomer composition including water-soluble ethylene-based unsaturated monomers having at least partially neutralized acidic groups; and
a water-soluble component,
wherein the water-soluble component has a weight average molecular weight of 150,000 to 250,000 g/mol,
wherein the water-soluble component has a content of 5 to 20 wt %, based on the total weight of the super absorbent polymer, as measured by the EDANA WSP 270.2 method; and
wherein a permeability of the super absorbent polymer measured according to the following Equation 1 is 10 to 150 seconds:

Permeability (sec)=$T1-B$ [Equation 1]

wherein T1 represents a time required for decreasing a liquid level height from 40 ml up to 20 ml under a load of 0.3 psi (106.26 g) in a chromatography tube in the presence of saline solution-absorbed super absorbent polymer, wherein the saline solution-absorbed super absorbed polymer is prepared by putting 0.2±0.0005 g of a classified sample (30 # to 50 #) (particles size ranging from 300 μm to 600 μm) of super absorbent polymer into the chromatography tube and adding saline solution so that the saline solution has a volume of 50 ml, and leaving the tube for 30 minutes prior to measuring T1, and B represents a time required for decreasing a liquid level height from 40 ml up to 20 ml in a chromatography tube filled with saline solution under a load of 0.3 psi in the absence of the super absorbent polymer;
wherein a centrifuge retention capacity is 30 to 35 g/g as measured by the EDANA WSP 241.2 method.

* * * * *